United States Patent
Nowottny et al.

(10) Patent No.: US 11,529,303 B2
(45) Date of Patent: Dec. 20, 2022

(54) METHOD FOR DYEING KERATINOUS MATERIAL, CONTAINING DYE AND AN ACIDIC POST-TREATMENT AGENT

(71) Applicant: Henkel AG & Co. KGaA, Duesseldorf (DE)

(72) Inventors: Marc Nowottny, Moenchengladbach (DE); Torsten Lechner, Langenfeld (DE); Sofie Baumann, Remscheid (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 0 days.

(21) Appl. No.: 17/415,618

(22) PCT Filed: Nov. 7, 2019

(86) PCT No.: PCT/EP2019/080583
§ 371 (c)(1),
(2) Date: Jun. 17, 2021

(87) PCT Pub. No.: WO2020/126204
PCT Pub. Date: Jun. 25, 2020

(65) Prior Publication Data
US 2022/0054395 A1     Feb. 24, 2022

(30) Foreign Application Priority Data
Dec. 18, 2018  (DE) .................. 10 2018 222 024.7

(51) Int. Cl.
| | |
|---|---|
| *A61Q 5/10* | (2006.01) |
| *A61K 8/898* | (2006.01) |
| *A61K 8/19* | (2006.01) |
| *A61K 8/365* | (2006.01) |
| *A61K 8/81* | (2006.01) |

(52) U.S. Cl.
CPC ............ *A61K 8/898* (2013.01); *A61K 8/19* (2013.01); *A61K 8/365* (2013.01); *A61K 8/817* (2013.01); *A61Q 5/10* (2013.01); *A61K 2800/43* (2013.01); *A61K 2800/884* (2013.01)

(58) Field of Classification Search
CPC . A61Q 5/10; A61Q 5/065; A61K 8/19; A61K 2800/88; A61K 2800/884; A61K 2800/43; A61K 8/25; A61K 8/898; A61K 8/365; A61K 8/817
USPC .......................................................... 8/405
See application file for complete search history.

(56) References Cited

U.S. PATENT DOCUMENTS

| | | | |
|---|---|---|---|
| 2005/0255075 A1 | 11/2005 | Meder et al. | |
| 2010/0083446 A1* | 4/2010 | Brun ............ | A61K 8/891 8/405 |
| 2013/0344021 A1* | 12/2013 | Meder ........... | A61Q 5/004 424/70.122 |
| 2017/0172901 A1* | 6/2017 | Kerl ............. | A61K 8/22 |

FOREIGN PATENT DOCUMENTS

| | | |
|---|---|---|
| DE | 102004013795 A1 | 10/2004 |
| DE | 102014218006 A1 | 3/2016 |

OTHER PUBLICATIONS

STIC Search Report dated Jan. 12, 2022.*
EPO, International Search Report issued in International Application No. PCT/EP2019/080583, dated Jan. 7, 2020.

* cited by examiner

*Primary Examiner* — Eisa B Elhilo
(74) *Attorney, Agent, or Firm* — Lorenz & Kopf, LLP

(57) ABSTRACT

A kit-of-parts and a process for dyeing keratinous material, such as human hair, are provided. The method includes applying a coloring agent (a) to the keratinous material, wherein the agent (a) includes (a1) at least one amino-functionalized silicone polymer, and (a2) at least one color-imparting compound, and (a3) optionally, a film-forming polymer different from (a1). The method further includes applying a post-treatment agent (b) to the keratinous material, wherein the agent (b) includes (b1) at least one acid, and (b2) optionally, a film-forming polymer. In the method, at least one of the agents (a) and/or (b) comprises at least one film-forming polymer.

19 Claims, No Drawings

METHOD FOR DYEING KERATINOUS MATERIAL, CONTAINING DYE AND AN ACIDIC POST-TREATMENT AGENT

CROSS-REFERENCE TO RELATED APPLICATION

This application is a U.S. National-Stage entry under 35 U.S.C. § 371 based on International Application No. PCT/EP2019/080583, filed Nov. 7, 2019, which was published under PCT Article 21(2) and which claims priority to German Application No. 10 2018 222 024.7, filed Dec. 18, 2018, which are all hereby incorporated in their entirety by reference.

TECHNICAL FIELD

The subject of the present application is a process for dyeing keratinous material, in particular human hair, which comprises the application of at least two different agents (a) and (b). The agent (a) comprises at least one amino-functionalized silicone polymer (a1) and at least one colorant compound (a2). The agent (b) is an acidic post-treatment agent. Furthermore, at least one of agents (a) and/or (b) contains a film-forming polymer.

The second subject of this application is a multi-component packaging unit (kit-of-parts) for coloring keratinous material, in particular human hair, which comprises the agents (a) and (b) separately packaged in two different containers.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing with good fastness properties and good grey coverage. Such colorants contain oxidation dye precursors, so-called developer components, and coupler components, which, under the influence of oxidizing agents such as hydrogen peroxide, form the actual dyes among themselves. Oxidation dyes are characterized by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyeing with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents containing surfactants. Various products of this type are available on the market under the name hair mascara.

If the user wants particularly long-lasting dyes, the use of oxidative dyes has so far been the only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes.

BRIEF SUMMARY

The purpose of the present disclosure was to provide a dyeing system with fastness properties comparable to those of oxidative dyeing. Wash fastness properties should be outstanding, but the use of oxidation dye precursors normally used for this purpose should be avoided. A technology was sought that would make it possible to fix the coloring compounds (such as pigments) known from the state of the art in an extremely durable way to the hair. When the agents are used in a dyeing process, intensive dyeing results with good fastness properties should be obtained. In particular, the application of the corresponding processes should result in particularly washfast colorations that do not suffer any weakening of the color intensity even after repeated combing or styling.

Surprisingly, it has now turned out that the above-mentioned task can be excellently solved if keratinous materials, especially hair, are dyed using a procedure in which at least two agents (a) and (b) are applied to the keratinous materials (hair). In this case, the agent (a) comprises at least one amino-functionalized silicone polymer (a1), at least one colorant compound (a2) and, if desired, at least one film-forming polymer (a3) other than (a1). The agent (b) represents an acidic aftertreatment agent and contains at least one acid (b1) and optionally at least one film-forming polymer (b2). Furthermore, in the case of both agents (a) and (b), there is the proviso that at least one of the agents (a) and/or (b) contains at least one film-forming polymer. When both agents (a) and (b) were used in a dyeing process, keratinous fibers could be dyed with high color intensity. In addition, the wash fastness of the hair dyed with (a) and (b) was excellent.

An exemplary embodiment provides a process for dyeing keratinous material, such as human hair. The method includes applying a coloring agent (a) to the keratinous material, wherein the agent (a) includes (a1) at least one amino-functionalized silicone polymer, and (a2) at least one color-imparting compound, and (a3) optionally, a film-forming polymer different from (a1). The method further includes applying a post-treatment agent (b) to the keratinous material, wherein the agent (b) includes (b1) at least one acid, and (b2) optionally, a film-forming polymer. In the method, at least one of the agents (a) and/or (b) comprises at least one film-forming polymer.

In another embodiment, a kit-of-parts is provided for dyeing keratinous material, such as human hair. The kit-of-parts includes a first container and a second container that are separately packaged. The first container contains a coloring agent (a), the agent comprising (a): (a1) at least one amino-functionalized silicone polymer, and (a2) at least one color-imparting compound, and (a3) optionally at least one film-forming polymer. The second container contains an agent (b), wherein the agent (b) comprises: (b1) at least one acid, and (b2) optionally, at least one film-forming polymer. In the kit-of-parts, at least one of the agents (a) and/or (b) comprises at least one film-forming polymer.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

A first object of the present disclosure is a method for coloring keratinous material, in particular human hair, comprising the following steps:

Application of a coloring agent (a) to the keratinous material, said agent (a) comprising:
(a1) at least one amino-functionalized silicone polymer, and
(a2) at least one color-imparting compound, and
(a3) optionally at least one film-forming polymer different from (a1), Application of a post-treatment agent (b) to the keratinous material, the agent (b) comprising:
(b1) at least one acid, and
(b2) optionally at least one film-forming polymer, with the proviso that at least one of the agents (a) and/or (b) comprises at least one film-forming polymer.

In the work leading to this present disclosure, it has been shown that the successive application of colorant (a) and aftertreatment agent (b) results in dyed keratinous material, which is exemplified by good fastness properties, by particularly good wash fastness properties.

Without being limited to this theory, it is believed that the amino-functionalized silicone polymer (a1) contained in the colorant (a) forms adhesive bonds with the keratin material, which initially fix the amino silicone (a1) to the keratin material. The colorant compounds (a2) are incorporated into or onto the amino silicone (a1) and are thus also immobilized on the outside of the keratin material.

The adhesive bonds between amino-functionalized silicone polymer (a1) and keratin are presumably based on electrostatic interactions formed between the positively charged amino groups of the silicone polymer (a1) and negative charges on the keratin material.

Surprisingly, it was observed that the color-imparting compounds (a2) attach to the latter or form a common layer with the amino silicone (a1) when used simultaneously. This joint layer formation of (a1) and (a2) means that dyeing with good wash fastness can be obtained, even without the need for diffusion of the colorant compound into the hair fiber. By using a film-forming polymer that is incorporated either into the colorant (a) and/or into the aftertreatment agent (b), the layer of (a1) and (a2) can be additionally fixed and the wash fastness further strengthened in this way.

Furthermore, it was found that when amino silicone (a1) and colorant compound (a2) were deposited together, very stable layers could be formed, especially when the optimized pH values were selected for the application. Particularly resistant coatings could be obtained if (a1) and (a2) were first applied to the keratin materials in a neutral to basic environment, and the pH was subsequently lowered by applying an acidic post-treatment agent.

Keratinic Material

Keratinous material includes hair, skin, nails (such as fingernails and/or toenails). Wool, furs, and feathers also fall under the definition of keratinous material. Preferably, keratinous material is understood to be human hair, human skin, and human nails, especially fingernails and toenails. Keratinous material is understood to be human hair.

Agents (a) and (b)

In the procedure as contemplated herein, agents (a) and (b) are applied to the keratinous material, in particular human hair. In exemplary embodiments, (a) and (b) are different.

In other words, a first subject of the present disclosure is a process for dyeing keratinous material, in particular human hair, comprising the following steps:

Application of a coloring agent (a) to the keratinous material, said agent (a) comprising:
(a1) at least one amino-functionalized silicone polymer, and
(a2) at least one color-imparting compound, and
(a3) optionally at least one film-forming polymer different from (a1), Application of a post-treatment agent (b) to the keratinous material, the agent (b) comprising:
(b1) at least one acid, and
(b2) optionally at least one film-forming polymer, provided that
at least one of the agents (a) and/or (b) comprises at least one film-forming polymer, and
the means (a) and (b) are different from each other.

Amino Functionalized Silicone Polymer (a1) in the Medium (a)

As the first ingredient (a1) essential to the present disclosure, the composition (a) comprises at least one amino-functionalized silicone polymer. The amino-functionalized silicone polymer may alternatively be referred to as amino silicone or amodimethicone.

Silicone polymers are generally macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size and is partly determined by the polymerization method. For the purposes of the present disclosure, it is preferred if the maximum molecular weight of the silicone polymer is not more than $10^7$ g/mol, preferably not more than $10^6$ g/mol, and particularly preferably not more than $10^5$ g/mol.

The silicone polymers comprise many Si-O repeating units, and the Si atoms may carry organic radicals such as alkyl groups or substituted alkyl groups. Alternatively, a silicone polymer is therefore also referred to as polydimethylsiloxane.

Corresponding to the high molecular weight of silicone polymers, these are based on more than 10 Si-O repeat units, preferably more than 50 Si-O repeat units, and more preferably more than 100 Si-O repeat units, most preferably more than 500 Si-O repeat units.

An amino-functionalized silicone polymer is understood to be a functionalized polydimethylsiloxane which carries at least one structural unit with an amino group. Preferably, the amino-functionalized silicone polymer carries multiple structural units, each having at least one amino group. An amino group is understood to mean a primary amino group, a secondary amino group, and a tertiary amino group. All these amino groups can be protonated in the acidic environment and are then present in their cationic form.

In principle, good effects could be obtained with amino-functionalized silicone polymers (a1) if they carry at least one primary, at least one secondary and/or at least one tertiary amino group. However, dyeing with the best wash fastness were observed when an amino-functionalized silicone polymer (a1) was used in agent (a), which contains at least one secondary amino group.

In a very particularly preferred embodiment, a process as contemplated herein is exemplified in that the agent (a)

comprises at least one amino-functionalized silicone polymer (a1) having at least one secondary amino group.

The secondary amino group(s) may be located at various positions on the amino-functionalized silicone polymer. Particularly good effects were found when an amino-functionalized silicone polymer (a1) was used that has at least one, preferably several, structural units of the formula (Si-Amino).

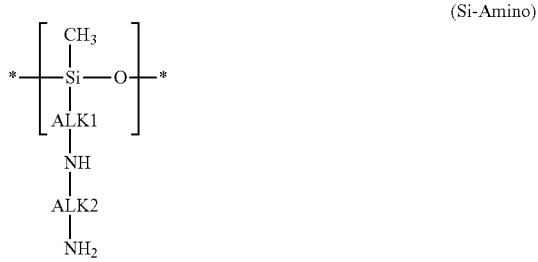
(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, a process as contemplated herein is exemplified in that the agent (a) comprises at least one amino-functionalized silicone polymer (a1) comprising at least one structural unit of the formula (SiAmino),

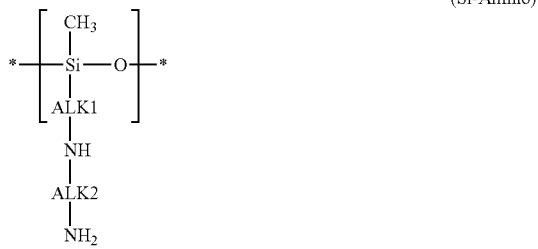
(Si-Amino)

Where ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A divalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear divalent $C_1$-$C_{20}$ alkylene group include the methylene group (—$CH_2$—), the ethylene group (—$CH_2$—$CH_2$—), the propylene group (—$CH_2$—$CH_2$—$CH_2$—) and the butylene group (—$CH_2$—$CH_2$—$CH_2$—$CH_2$—). The propylene group (—$CH_2$—$CH_2$—$CH_2$—) is particularly preferred. From a chain length of 3 C atoms, divalent alkylene groups can also be branched. Examples of branched divalent $C_3$-$C_{20}$ alkylene groups are (—$CH_2$—CH($CH_3$)—) and (—$CH_2$—CH($CH_3$)—$CH_2$—).

In another particularly preferred embodiment, the structural units of the formula (SiAmino) represent repeat units in the amino-functionalized silicone polymer (a1), so that the silicone polymer comprises multiple structural units of the formula (SiAmino)

Particularly well-suited amino-functionalized silicone polymers (a1) with at least one secondary amino group are listed below.

Dyeing with the absolute best wash fastnesses could be obtained if in the process as contemplated herein at least one agent (a) was applied to the keratinous material which contains at least one amino-functionalized silicone polymer (a1) comprising structural units of the formula (Si-I) and of the formula (Si-II)

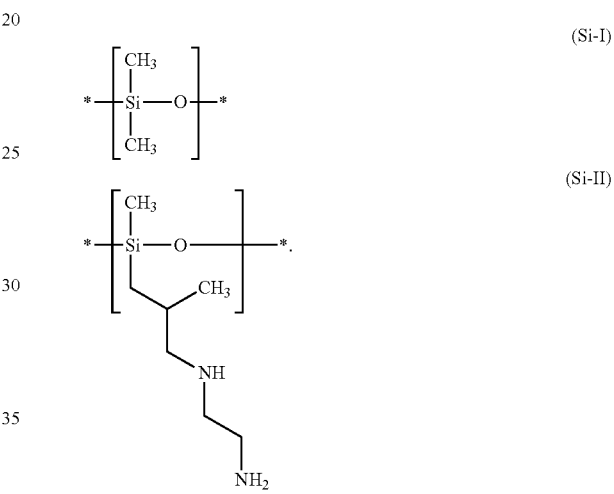

In a further quite particularly preferred embodiment, a process as contemplated herein is exemplified in that the agent (a) contains at least one amino-functionalized silicone polymer (a1) which comprises structural units of the formula (Si-I) and of the formula (Si-II)

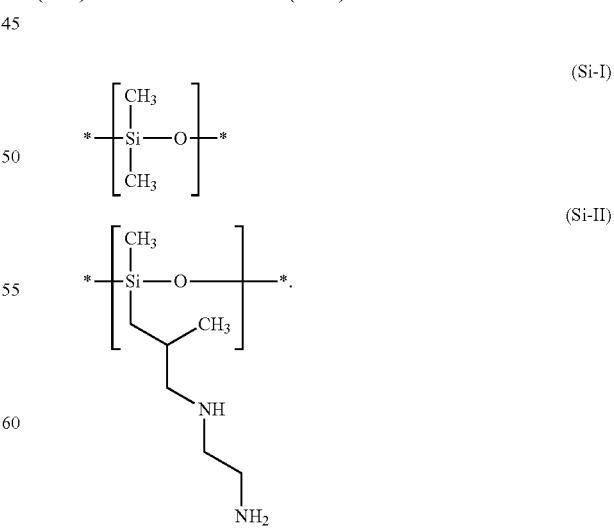

A corresponding amino-functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[2-aminoethyl)amino]-2-methylpropyl Me, Di-Me-Siloxane" and the CAS number 106842-44-8.

In the context of a further preferred embodiment, a process as contemplated herein is exemplified by the application of an agent (a) to the keratinous material, the agent (a) comprising at least one amino-functional silicone polymer (a1) of the formula of formula (Si-III),

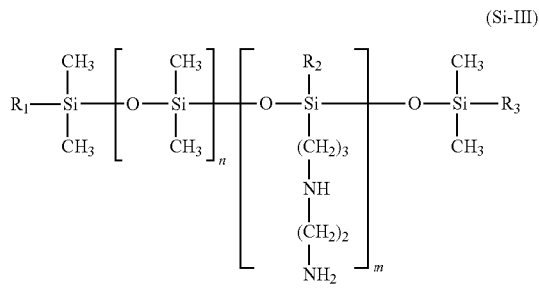

where
  m and n mean numbers chosen so that the sum (n+m) is in the range of about 1 to about 1000,
  n is a number in the range of about 0 to about 999 and m is a number in the range of about 1 to about 1000,
  R1, R2 and R3, which are the same or different, denote a hydroxy group or a C1-4 alkoxy group,
  wherein at least one of R1 to R3 represents a hydroxy group;

Further methods preferred as contemplated herein are exemplified by the application of an agent (a) to the keratinous material, the agent (a) comprising at least amino-functional silicone polymer (a1) of the formula of formula (Si-IV),

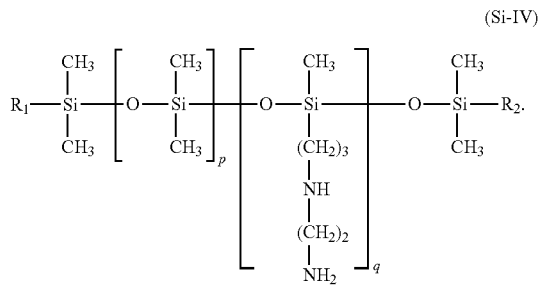

wherein
  p and q mean numbers chosen so that the sum (p+q) is in the range of about 1 to about 1000,
  p is a number in the range of about 0 to about 999 and q is a number in the range of 1 to about 1000,
  R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si-atom, which carries the nitrogen-containing group: In formula (Si-III), R2 represents a hydroxy group or a C1-4 alkoxy group, while the residue in formula (Si-IV) is a methyl group. The individual Si groupings, which are marked with the indices m and n or p and q, do not have to be present as blocks; rather, the individual units can also be present in a statistically distributed manner, i.e., in the formulas (Si-III) and (Si-IV), not every R1-Si(CH$_3$)$_2$ group is necessarily bonded to an —[O—Si(CH$_3$)$_2$] grouping.

Processes as contemplated herein in which an agent (a) containing at least one amino-functional silicone polymer (a1) of the formula of the formula (Si-V) is applied to the keratin fibers have also proved to be particularly effective with respect to the desired effects

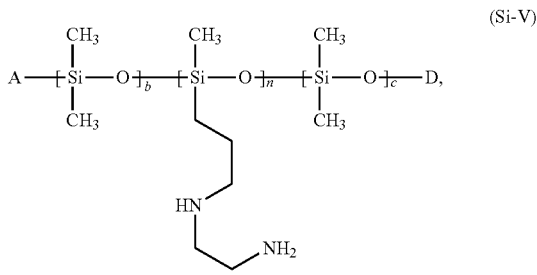

wherein
A represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
b, n, and c stand for integers between 0 and 1000,
with the specifications that
  n>0 and b+c>0
  at least one of the conditions A=—OH or D=—H is fulfilled.

In the above formula (Si-V), the individual siloxane units are statistically distributed with the indices b, c, and n, i.e., they do not necessarily have to be block copolymers.

Agent (a) may further comprise one or more different amino-functionalized silicone polymers represented by the formula (Si-VI)

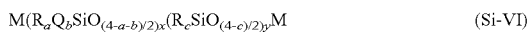

in which formula above, R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical containing at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2. 000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3-chloropropyl, 4-bromobutyl, 3,3,3-trifluoropropyl, chlorocyclohexyl, bromophenyl, chlorophenyl and the like, and sulfur-containing radicals, such as mercaptoethyl, mercaptopropyl, mercaptohexyl, mercaptophenyl and the like; preferably R is an alkyl radical containing from 1 to about 6 carbon atoms, and most preferably R is methyl. Examples of $R^1$ include methylene, ethylene, propylene, hexamethylene, decamethylene, —$CH_2CH(CH_3)CH_2$—, phenylene, naphthylene, —$CH_2CH_2SCH_2CH_2$—, —$CH_2CH_2OCH_2$—, —$OCH_2CH_2$—, —$OCH_2CH_2CH_2$—, —$CH_2CH(CH_3)C(O)OCH_2$—, —$(CH_2)_3CC(O)OCH_2CH_2$—, —$C_6H_4C_6H_4$—, —$C_6H_4CH_2C_6H_4$—; and —$(CH_2)_3C(O)SCH_2CH_2$—.

Z is an organic amino functional residue containing at least one amino functional group. One possible formula for Z is $NH(CH_2)_zNH_2$, where z is 1 or more. Another possible formula for Z is —$NH(CH_2)_z(CH_2)_{zz}NH$, wherein both z and zz are independently 1 or more, this structure comprising diamino ring structures, such as piperazinyl. Z is most preferably an —$NHCH_2CH_2NH_2$ residue. Another possible formula for Z is —$N(CH_2)_z(CH_2)_{zz}NX2$ or —$NX_2$, wherein each X of $X_2$ is independently selected from the group consisting of hydrogen and alkyl groups having 1 to 12 carbon atoms, and zz is 0.

Q is most preferably a polar, amine-functional radical of the formula —$CH_2CH_2CH_2NHCH_2CH_2NH_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of $R_aQ_bSiO_{(4-a-b)/2}$ units to $R_cSiO_{(4-c)/2}$ units is in the range of about 1:2 to about 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a method as contemplated herein is exemplified by the application of an agent (a) to the keratinous material, wherein the agent (a) contains an amino-functional silicone polymer of formula (Si-VII)

$$R'_aG_{3-a}\text{-Si}(OSiG_2)_n\text{-}(OSiG_bR'_{2-b})_m\text{—O—}SiG_{3-a}\text{-}R'_a \quad \text{(Si-VII)},$$

wherein:
G is —H, a phenyl group, OH, —O—$CH_3$, —$CH_3$, —O—$CH_2CH_3$, —$CH_2CH_3$, —O—$CH_2CH_2CH_3$, —$CH_2CH_2CH_3$, —O—$CH(CH_3)_2$, —$CH(CH_3)_2$, —O—$CH_2CH_2CH_2CH_3$, —$CH_2CH_2CH_2CH_3$, —O—$CH_2CH(CH_3)_2$, —$CH_2CH(CH_3)_2$, —O—$CH(CH_3)CH_2CH_3$, —$CH(CH_3)CH_2CH_3$, —O—$C(CH_3)_3$, —$C(CH_3)_3$;
a stands for a number between about 0 and about 3, especially 0;
b stands for a number between about 0 and about 1, especially 1,
m and n are numbers whose sum (m+n) is between about 1 and about 2000, preferably between about 50 and about 150, where n preferably assumes values from about 0 to about 1999 and from about 49 to about 149 and m preferably assumes values from about 1 to about 2000, from about 1 to about 10,
R' is a monovalent radical selected from

-Q-N(R")—$CH_2$—$CH_2$—N(R")$_2$

-Q-N(R")$_2$

-Q-N$^+$(R")$_3$A$^-$

-Q-N$^+$H(R")$_2$A$^-$

-Q-N$^+$H$_2$(R")A$^-$

-Q-N(R")—$CH_2$—$CH_2$—N$^+$R"H$_2$A$^-$ where each Q is a chemical bond, —$CH_2$—, —$CH_2$—$CH_2$—, —$CH_2CH_2CH_2$—, —$C(CH_3)_2$—, —$CH_2CH_2CH_2CH_2$—, —$CH_2C(CH_3)_2$—, —$CH(CH_3)CH_2CH_2$—,
R" represents identical or different radicals selected from the group consisting of —H, -phenyl, -benzyl, —$CH_2$—CH$(CH_3)$Ph, the $C_{1-20}$ alkyl radicals, preferably —$CH_3$, —$CH_2CH_3$, —$CH_2CH_2CH_3$, —$CH(CH_3)_2$, —$CH_2CH_2CH_2H_3$, —$CH_2CH(CH_3)_2$, —$CH(CH_3)CH_2CH_3$, —$C(CH_3)_3$, and A represents an anion preferably selected from chloride, bromide, iodide or methosulfate.

In the context of a further preferred embodiment, a process as contemplated herein is exemplified by the application of an agent (a) to the keratinous material, the agent (a) comprising at least one amino-functional silicone polymer (a1) of the formula (Si-VIIa),

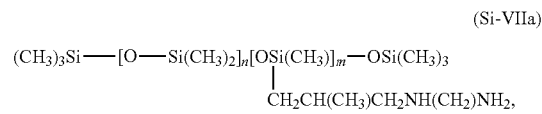
(Si-VIIa)

wherein m and n are numbers whose sum (m+n) is between about 1 and about 2000, preferably between about 50 and about 150, n preferably assuming values from about 0 to about 1999 and from about 49 to about 149, and m preferably assuming values from about 1 to about 2000, from about 1 to about 10.

According to the INCI declaration, these silicones are called trimethylsilylamodimethicones.

In another preferred embodiment, a method as contemplated herein is exemplified by the application of an agent (a) to the keratinous material, said agent (a) comprising at least one amino-functional silicone polymer of formula (Si-VIIb)

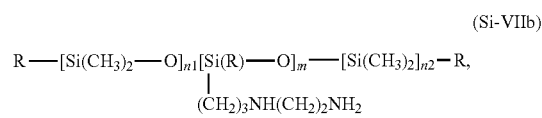
(Si-VIIb)

in which R represents —OH, —O—$CH_3$ or a —$CH_3$ group and m, n1 and n2 are numbers whose sum (m+n1+n2) is between about 1 and about 2000, preferably between about 50 and about 150, the sum (n1+n2) preferably assuming values from about 0 to about 1999 and from about 49 to about 149 and m preferably assuming values from about 1 to about 2000, from about 1 to about 10.

According to the INCI declaration, these amino-functionalized silicone polymers are called amodimethicones.

Regardless of which amino-functional silicones are used, agents (a) as contemplated herein are preferred which contain an amino-functional silicone polymer whose amine number is above 0.25 meq/g, preferably above 0.3 meq/g, such as above 0.4 meq/g. The amine number represents the milliequivalents of amine per gram of the amino-functional silicone. The amine number represents the milliequivalents of amine per gram of the amino-functional silicone.

Furthermore, agents (a) which contained a special 4-morpholinomethyl-substituted silicone polymer (a1) are also suitable for use in the process as contemplated herein. This amino-functionalized silicone polymer comprises structural units of the formulae (SI-VIII) and of the formula (Si-IX)

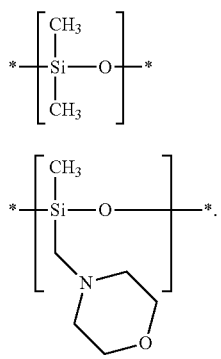

Corresponding 4-morpholinomethyl-substituted silicone polymers are described below.

A very particularly preferred amino-functionalized silicone polymer is known by the name of
Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

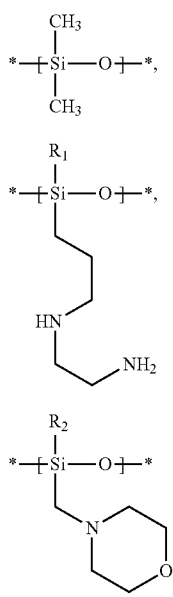

in which
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.

Particularly preferred compositions (a) as contemplated herein contain at least one 4-morpholinomethyl-substituted silicone of the formula (Si-XI)

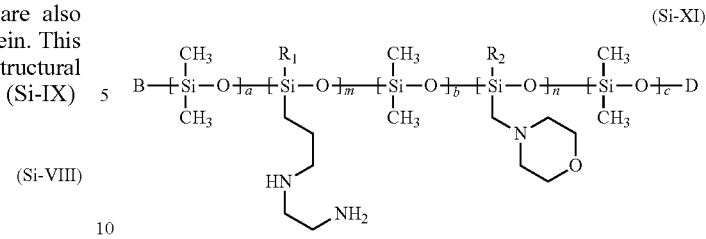

wherein
R1 is —CH$_3$, —OH, —OCH$_3$, —O—CH$_2$CH$_3$, —O—CH$_2$CH$_2$CH$_3$, or —O—CH(CH$_3$)$_2$;
R2 is —CH$_3$, —OH, or —OCH$_3$.
B represents a group —OH, —O—Si(CH$_3$)$_3$, —O—Si(CH$_3$)$_2$OH, —O—Si(CH$_3$)$_2$OCH$_3$,
D represents a group —H, —Si(CH$_3$)$_3$, —Si(CH$_3$)$_2$OH, —Si(CH$_3$)$_2$OCH$_3$,
a, b, and c stand independently for integers between 0 and 1000, with the condition a+b+c>0
m and n independently of each other stand for integers between 1 and 1000
with the proviso that
at least one of the conditions B=—OH or D=—H is fulfilled,
the units a, b, c, m, and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e., the terminal grouping B or D is preferably attached to a dimethylsiloxy grouping. Also, in formula (Si-VI), the siloxane units a, b, c, m, and n are preferably statistically distributed.

The silicones used as contemplated herein represented by formula (Si-VI) can be trimethylsilyl-terminated (D or B=—Si(CH3)3), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—Si(CH$_3$)$_2$OH and D=—Si(CH$_3$)$_3$
B=—O—Si(CH$_3$)$_2$OH and D=—Si(CH$_3$)$_2$OH
B=—O—Si(CH$_3$)$_2$OH and D=—Si(CH$_3$)$_2$OCH$_3$
B=—O—Si(CH$_3$)$_3$ and D=—Si(CH$_3$)$_2$OH
B=—O—Si(CH$_3$)$_2$CH$_3$ and D=—Si(CH$_3$)$_2$OH. These silicones lead to exorbitant improvements in the hair properties of the hair treated with the agents of the present disclosure, and to a seriously improved protection in oxidative treatment.

To produce particularly resistant films, the agent (a) contains the amino-functionalized silicone polymer(s) (a2), preferably in certain ranges of amounts.

Particularly robust films were obtained when an agent (a) was used in the process as contemplated herein which contains—based on the total weight of the agent (a)—one or more silicone polymers in a total amount of from about 0.1 to about 8.0% by weight, preferably from about 0.02 to about 5.0% by weight, more preferably from about 0.1 to about 3.0% by weight, and very particularly preferably from about 0.05 to about 3.5% by weight.

In a further preferred embodiment, a process as contemplated herein is exemplified in that the agent (a) contains—based on the total weight of the agent (a)—one or more amino-functionalized silicone polymers in a total amount of from about 0.1 to about 8.0% by weight, preferably from about 0.02 to about 5.0% by weight, more preferably from about 0.1 to about 3.0% by weight, and very preferably from about 0.05 to about 3.5% by weight.

Colorant Compound (a2) in the Medium (a)

As a second constituent essential to the present disclosure, the agent (a) used in the process as contemplated herein contains at least one color-imparting compound (a2).

For the purposes of the present disclosure, colorant compounds are substances capable of imparting a coloration to the keratin material. Particularly well-suited colorant compounds can be selected from the group of pigments, direct-acting dyes, photochromic dyes, and thermochromic dyes.

In a further preferred embodiment, a process as contemplated herein is exemplified in that the agent (a) comprises at least one colorant compound (a2) from the group consisting of pigments, direct dyes, photochromic dyes, and thermochromic dyes.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A stir-fish is added. Then one liter of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, an agent (a) as contemplated herein is exemplified in that it contains at least one colorant compound (a2) from the group consisting of inorganic and/or organic pigments.

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-containing silicates, silicates, metal sulfides, complex metal cyanides, metal sulphates, chromates and/or molybdates. Preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510)r and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidoliter and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein is exemplified in that the agent (a) comprises at least one colorant compound (a2) from the group of inorganic pigments, which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a composition as contemplated herein is exemplified in that it comprises (a) at least one colorant compound (a2) from the group of pigments selected from mica- or mica-based pigments which are reacted with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:

Colorona Copper, Merck, MICA, CI 77491 (IRON OXIDES)

Colorona Passion Orange, Merck, Mica, CI 77491 (Iron Oxides), Alumina

Colorona Patina Silver, Merck, MICA, CI 77499 (IRON OXIDES), CI 77891 (TITANIUM DIOXIDE)

Colorona RY, Merck, CI 77891 (TITANIUM DIOXIDE), MICA, CI 75470 (CARMINE)

Colorona Oriental Beige, Merck, MICA, CI 77891 (TITANIUM DIOXIDE), CI 77491 (IRON OXIDES)

Colorona Dark Blue, Merck, MICA, TITANIUM DIOXIDE, FERRIC FERROCYANIDE

Colorona Chameleon, Merck, CI 77491 (IRON OXIDES), MICA

Colorona Aborigine Amber, Merck, MICA, CI 77499 (IRON OXIDES), CI 77891 (TITANIUM DIOXIDE)

Colorona Blackstar Blue, Merck, CI 77499 (IRON OXIDES), MICA

Colorona Patagonian Purple, Merck, MICA, CI 77491 (IRON OXIDES), CI 77891 (TITANIUM DIOXIDE), CI 77510 (FERRIC FERROCYANIDE)

Colorona Red Brown, Merck, MICA, CI 77491 (IRON OXIDES), CI 77891

-continued (TITANIUM DIOXIDE)
Colorona Russet, Merck, CI 77491 (TITANIUM DIOXIDE), MICA, CI 77891
(IRON OXIDES)
Colorona Imperial Red, Merck, MICA, TITANIUM DIOXIDE (CI 77891),
D&C RED NO. 30 (CI 73360)
Colorona Majestic Green, Merck, CI 77891 (TITANIUM DIOXIDE), MICA,
CI 77288 (CHROMIUM OXIDE GREENS)
Colorona Light Blue, Merck, MICA, TITANIUM DIOXIDE (CI 77891),
FERRIC FERROCYANIDE (CI 77510)
Colorona Red Gold, Merck, MICA, CI 77891 (TITANIUM DIOXIDE), CI 77491
(IRON OXIDES)
Colorona Gold Plus MP 25, Merck, MICA, TITANIUM DIOXIDE (CI 77891),
IRON OXIDES (CI 77491)
Colorona Carmine Red, Merck, MICA, TITANIUM DIOXIDE, CARMINE
Colorona Blackstar Green, Merck, MICA, CI 77499 (IRON OXIDES)
Colorona Bordeaux, Merck, MICA, CI 77491 (IRON OXIDES)
Colorona Bronze, Merck, MICA, CI 77491 (IRON OXIDES)
Colorona Bronze Fine, Merck, MICA, CI 77491 (IRON OXIDES)
Colorona Fine Gold MP 20, Merck, MICA, CI 77891 (TITANIUM DIOXIDE),
CI 77491 (IRON OXIDES)
Colorona Sienna Fine, Merck, CI 77491 (IRON OXIDES), MICA
Colorona Sienna, Merck, MICA, CI 77491 (IRON OXIDES)
Colorona Precious Gold, Merck, Mica, CI 77891 (Titanium dioxide), Silica,
CI 77491 (Iron oxides), Tin oxide
Colorona Sun Gold Sparkle MP 29, Merck, MICA, TITANIUM DIOXIDE,
IRON OXIDES, MICA, CI 77891, CI 77491 (EU)
Colorona Mica Black, Merck, CI 77499 (Iron oxides), Mica, CI 77891
(Titanium dioxide)
Colorona Bright Gold, Merck, Mica, CI 77891 (Titanium dioxide), CI 77491
(Iron oxides)

Colorona Blackstar Gold, Merck, MICA, CI 77499 (IRON OXIDES)

Other particularly preferred color pigments with the trade name Xirona® are for example:

Xirona Golden Sky, Merck, Silica, CI 77891 (Titanium Dioxide), Tin Oxide

Xirona Caribbean Blue, Merck, Mica, CI 77891 (Titanium Dioxide), Silica, Tin Oxide Xirona Kiwi Rose, Merck, Silica, CI 77891 (Titanium Dioxide), Tin Oxide Xirona Magic Mauve, Merck, Silica, CI 77891 (Titanium Dioxide), Tin Oxide.

In addition, particularly preferred color pigments with the trade name Unipure® are for example:

Unipure Red LC 381 EM, Sensient CI 77491 (Iron Oxides), Silica

Unipure Black LC 989 EM, Sensient, CI 77499 (Iron Oxides), Silica

Unipure Yellow LC 182 EM, Sensient, CI 77492 (Iron Oxides), Silica

In a further embodiment, the composition as contemplated herein may also comprise (a) one or more colorant compounds (a2) from the group consisting of organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolopyrrole, indigo, thioindido, dioxazine, and/or triarylmethane compounds.

Examples of particularly suitable organic pigments are carmine, quinacridone, phthalocyanine, sorghum, blue pigments with the Color Index numbers Cl 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a process as contemplated herein is exemplified in that the composition (a) comprises at least one colorant compound (a2) from the group of organic pigments selected from the group consisting of carmine, quinacridone, phthalocyanine, sorghum, blue pigments having the color index numbers Cl 42090, CI 69800, CI 69825, CI 73000, CI 74100, CI 74160, yellow pigments having the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above-mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the agent (a) of the process as contemplated herein is particularly preferred. It is also preferred if the pigments used have a certain particle size. As contemplated herein, it is therefore advantageous if the at least one pigment has an average particle size D50 of about 1.0 to about 50 µm, preferably from about 5.0 to about 45 µm, preferably from about 10 to about 40 µm, 14 to about 30 µm. The mean particle size $D50D_{50}$, for example, can be determined using dynamic light scattering (DLS).

The pigment or pigments may be used in an amount of from about 0.001 to about 20% by weight, or from about 0.05 to about 5% by weight, based in each case on the total weight of the agent (a).

As colorant compounds (a2), the agents (a) used in the process as contemplated herein may also contain one or more direct dyes. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes, or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1.0 g/L.

Direct dyes can be divided into anionic, cationic, and non-ionic direct dyes.

In a further preferred embodiment, a process as contemplated herein is exemplified in that the agent (a) comprises at least one colorant compound (a2) from the group including anionic, nonionic, and cationic direct dyes.

Suitable cationic direct dyes include Basic Blue 7, Basic Blue 26, HC Blue 16, Basic Violet 2, and Basic Violet 14, Basic Yellow 57, Basic Red 76, Basic Blue 16, Basic Blue 347 (Cationic Blue 347/Dystar), HC Blue No. 16, Basic Blue 99, Basic Brown 16, Basic Brown 17, Basic Yellow 57, Basic Yellow 87, Basic Orange 31, Basic Red 51, and Basic Red 76.

As non-ionic direct dyes, non-ionic nitro and quinone dyes and neutral azo dyes can be used. Suitable non-ionic direct dyes are those listed under the international designations or Trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol 2-(2-hydroxyethyl)amino-4,6-dinitrophenol, 4-[(2-hydroxyethyl)amino]-3-nitro-1-methylbenzene, 1-amino-4-(2-hydroxyethyl)-amino-5-chloro-2-nitrobenzene, 4-amino-3-nitrophenol, 1-(2'-ureidoethyl)amino-4-nitrobenzene, 2-[4-amino-2-nitrophenyl)amino]benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

In the course of the work leading to the present disclosure, it has been found that dyeing with good color intensities and fastness properties can also be produced with agents (a) containing at least one anionic direct dye (a2).

In a further embodiment, a process as contemplated herein is therefore exemplified in that the agent (a) comprises at least one anionic direct dye.

Anionic direct dyes are also called acid dyes. Acid dyes are direct dyes that have at least one carboxylic acid group ($-COOH$) and/or one sulphonic acid group ($-SO_3H$). Depending on the pH value, the protonated forms ($-COOH$, $-SO_3H$) of the carboxylic acid or sulphonic acid groups are in equilibrium with their deprotonated forms ($-OO^-$, $-SO_3^-$ present). The proportion of protonated forms increases with decreasing pH value. If direct dyes are used in the form of their salts, the carboxylic acid groups or sulphonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulphonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes, and/or indophenol dyes.

In one embodiment, a process for dyeing keratinous material is thus preferred, which is exemplified in that the composition (a) comprises at least one anionic direct dye selected from the group consisting of nitrophenylenediamines, nitroaminophenols, azo dyes, anthraquinone dyes, triarylmethane dyes, xanthene dyes, rhodamine dyes, oxazine dyes and/or indophenol dyes, the xanthene dyes, the rhodamine dyes, the oxazine dyes and/or the indophenol dyes, the dyes from the abovementioned group each having at least one carboxylic acid group ($-COOH$), a sodium carboxylate group ($-COONa$), a potassium carboxylate group ($-COOK$), a sulfonic acid group ($-SO_3H$), a sodium sulfonate group ($-SO_3Na$), and/or a potassium sulfonate group ($-SO_3K$).

For example, one or more compounds from the following group can be selected as particularly well suited acid dyes: Acid Yellow 1 (D&C Yellow 7, Citronin A, Ext. D&C Yellow No. 7, Japan Yellow 403,CI 10316, COLIPA no B001), Acid Yellow 3 (COLIPA no: C 54, D&C Yellow No 10, Quinoline Yellow, E104, Food Yellow 13), Acid Yellow 9 (CI 13015), Acid Yellow 17 (CI 18965), Acid Yellow 23 (COLIPA no C 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA no C015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1; CI 20170; KATSU201; nosodiumsalt; Brown No. 201; RESORCIN BROWN; ACID ORANGE 24; Japan Brown 201; D & C Brown No. 1), Acid Red 14 (C.I. 14720), Acid Red 18 (E124, Red 18; CI 16255), Acid Red 27 (E 123, CI 16185, C-Rot 46, Echtrot D, FD&C Red Nr. 2, Food Red 9, Naphtholrot S), Acid Red 33 (Red 33, Fuchsia Red, D&C Red 33, CI 17200), Acid Red 35 (CI C.I. 18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red no 106 Pontacyl Brilliant Pink), Acid Red 73 (CI 27290), Acid Red 87 (Eosin, CI 45380), Acid Red 92 (COLIPA no C53, CI 45410), Acid Red 95 (CI 45425, Erythtosine, Simacid Erythrosine Y), Acid Red 184 (CI 15685), Acid Red 195, Acid Violet 43 (Jarocol Violet 43, Ext. D&C Violet no 2, C.I. 60730, COLIPA no C063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black no 401, Naphthalene Black 10B, Amido Black 10B, CI 20 470, COLIPA no B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

For example, the water solubility of anionic direct dyes can be determined in the following way. 0.1 g of the anionic direct dye is placed in a beaker. A stir-fish is added. Then add 100 ml of water. This mixture is heated to 25° C. on a magnetic stirrer while stirring. It is stirred for 60 minutes. The aqueous mixture is then visually assessed. If there are still undissolved residues, the amount of water is increased—for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyeazo)-1H-pyrazole-3-carboxylic acid and is highly soluble in water at 25° C.

Acid Orange 7 is the sodium salt of 4-[(2-hydroxy-1-naphthyl)azo]benzene sulphonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high-water solubility of more than 20% by weight.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)-benzenesulfonate and has a solubility in water of more than 20% by weight (25° C.).

In a further embodiment, a process as contemplated herein is therefore exemplified in that the agent (a) comprises at least one direct dye (a2) selected from the group consisting of Acid Yellow 1, Acid Yellow 3, Acid Yellow 9, Acid Yellow 17, Acid Yellow 23, Acid Yellow 36, Acid Yellow 121, Acid Orange 6, Acid Orange 7, Acid Orange 10, Acid Orange 11, Acid Orange 15, Acid Orange 20, Acid Orange 24, Acid Red 14, Acid Red, Acid Red 27, Acid Red 33, Acid Red 35, Acid Red 51, Acid Red 52, Acid Red 73, Acid Red 87, Acid Red 92, Acid Red 95, Acid Red 184, Acid Red 195, Acid Violet 43, Acid Violet 49, Acid Violet 50, Acid Blue 1, Acid Blue 3, Acid Blue 7, Acid Blue 104, Acid Blue 9, Acid Blue 62, Acid Blue 74, Acid Blue 80, Acid Green 3, Acid Green 5, Acid Green 9, Acid Green 22, Acid Green 25, Acid Green 50, Acid Black 1, Acid Black 52, Food Yellow 8, Food Blue 5, D&C Yellow 8, D&C Green 5, D&C Orange 10, D&C Orange 11, D&C Red 21, D&C Red 27, D&C Red 33, D&C Violet 2, and/or D&C Brown 1.

The direct dye(s) can be used in different amounts in the medium (a), depending on the desired color intensity. Particularly good results could be obtained if the agent (a)—based on the total weight of the agent (a)—contains one or more direct dyes (b) in a total amount of from about 0.01 to about 10.0% by weight, preferably from about 0.1 to about 8.0% by weight, more preferably from about 0.2 to about 6.0% by weight and most preferably from about 0.5 to about 4.5% by weight.

Furthermore, the agent (a) may also contain at least one photochromic or thermochromic dye as the coloring compound (a2).

Photochromic dyes are dyes that react to irradiation with UV light (sunlight or black light) with a reversible change in hue. In the process, the UV light changes the chemical structure of the dyes and thus their absorption behavior (Photochromic).

Thermochromic dyes are dyes that react to temperature changes with a reversible change in hue. In this process, the change in temperature alters the chemical structure of the dyes and thus their absorption behavior (Thermochromism).

The agent (a) may contain—based on the total weight of the agent (a)—one or more photochromic dyes (b) in a total amount of from about 0.01 to about 10.0% by weight, preferably from about 0.1 to about 8.0% by weight, more preferably from about 0.2 to about 6.0% by weight and most preferably from about 0.5 to about 4.5% by weight The agent (a) may contain—based on the total weight of the agent (a)—one or more thermochromic dyes (b) in a total amount of from about 0.01 to about 10.0% by weight, preferably from about 0.1 to about 8.0% by weight, more preferably from about 0.2 to about 6.0% by weight and very preferably from about 0.5 to about 4.5% by weight Film-Forming Polymer (a3) in the Medium (a)

When using the process as contemplated herein, it is a requirement that at least one of the agents (a) and/or (b) contains at least one film-forming polymer.

If the agent (a) contains at least one film-forming polymer, this is referred to below as (a3). If the agent (b) contains at least one film-forming polymer, this is referred to below as (b2).

It is particularly preferred if the agent (a) contains at least one film-forming polymer (a3). It is particularly preferred if the agent (a) contains at least one hydrophilic, film-forming polymer (a3). The film-forming polymer (a3) is different from the amino-functionalized silicone polymers (a1).

Furthermore, very particularly preferred is a process for coloring keratinous material, in particular human hair, comprising the following steps:
Application of a coloring agent (a) to the keratinous material, said agent (a) comprising:
(a1) at least one amino-functionalized silicone polymer, and
(a2) at least one color-imparting compound, and
(a3) at least one film-forming polymer different from (a1), and
Application of a post-treatment agent (b) to the keratinous material, the agent (b) comprising:
(b1) at least one acid.

Quite particularly preferred is a process for coloring keratinous material, in particular human hair, comprising the following steps:
Application of a coloring agent (a) to the keratinous material, said agent (a) comprising:
(a1) at least one amino-functionalized silicone polymer, and
(a2) at least one color-imparting compound, and
(a3) at least one film-forming hydrophilic polymer different from (a1), and
Application of a post-treatment agent (b) to the keratinous material, the agent (b) comprising:
(b1) at least one acid.

Polymers are macromolecules with a molecular weight of at least 1000 g/mol, preferably of at least 2500 g/mol, particularly preferably of at least 5000 g/mol, which include identical, repeating organic units. The polymers of the present disclosure may be synthetically produced polymers which are manufactured by polymerization of one type of monomer or by polymerization of different types of monomer which are structurally different from each other. If the polymer is produced by polymerizing a type of monomer, it is called a homo-polymer. If structurally different monomer types are used in polymerization, the resulting polymer is called a copolymer.

The maximum molecular weight of the polymer depends on the degree of polymerization (number of polymerized monomers) and the batch size and is determined by the polymerization method. For the purposes of the present disclosure, it is preferred that the maximum molecular weight of the film-forming hydrophobic polymer (c) is not more than $10^7$ g/mol, preferably not more than $10^6$ g/mol and particularly preferably not more than $10^5$ g/mol.

A hydrophilic polymer is a polymer that has a solubility in water at 25° C. (760 mmHg) of more than 1% by weight, preferably more than 2% by weight.

The water solubility of the film-forming, hydrophilic polymer can be determined in the following way, for example. 1.0 g of the polymer is placed in a beaker. Make up to 100 g with water. A stir-fish is added, and the mixture is heated to 25° C. on a magnetic stirrer while stirring. It is stirred for 60 minutes. The aqueous mixture is then visually assessed. A completely dissolved polymer appears macroscopically homogeneous. If the polymer-water mixture cannot be assessed visually due to a high turbidity of the mixture, the mixture is filtered. If no undissolved polymer remains on the filter paper, the solubility of the polymer is more than 1% by weight.

As contemplated herein, a film-forming polymer is a polymer which can form a film on a substrate, for example on a keratinic material or a keratinic fiber. The formation of a film can be demonstrated, for example, by looking at the keratin material treated with the polymer under a microscope.

Nonionic, anionic, and cationic polymers can be used as film-forming, hydrophilic polymers. The use of non-ionic, film-forming, hydrophilic polymers (a3) has proved to be particularly preferred.

In another very particularly preferred embodiment, a process as contemplated herein is exemplified in that the agent (a) comprises at least one nonionic, film-forming, hydrophilic polymer (a3).

Suitable film-forming hydrophilic polymers can be selected, for example, from the group of polyvinylpyrrolidone (co)polymers, polyvinyl alcohol (co)polymers, vinyl acetate (co)polymers, carboxyvinyl (co)polymers, acrylic acid (co)polymers, methacrylic acid (co)polymers, natural gums, polysaccharides, and/or acrylamide (co)polymers.

Furthermore, it is particularly preferred to use polyvinylpyrrolidone (PVP) and/or a vinylpyrrolidone-containing copolymer as film-forming hydrophilic polymer.

In another very particularly preferred embodiment, a process as contemplated herein is exemplified in that the agent (a) comprises at least one film-forming polymer (a3) selected from the group consisting of polyvinylpyrrolidone (PVP) and the copolymers of polyvinylpyrrolidone.

In another very particularly preferred embodiment, a process as contemplated herein is exemplified in that the agent (a) comprises at least one film-forming polymer (a3) selected from the group consisting of polyvinylpyrrolidone (PVP) and the copolymers of polyvinylpyrrolidone.

In certain embodiments, it is most preferred if the agent as contemplated herein contains polyvinylpyrrolidone (PVP) as the film-forming hydrophilic polymer (a3). Surprisingly, the wash fastness of the dyeing obtained with formulations containing PVP was particularly good.

Particularly well-suited polyvinylpyrrolidones are available, for example, under the name Luviskol® K from BASF SE, especially Luviskol® K 90 or Luviskol® K 85 from BASF SE.

The polymer PVP K30, which is marketed by Ashland (ISP, POI Chemical), can also be used as another very well suited polyvinylpyrrolidone (PVP). PVP K 30 is a polyvinylpyrrolidone which is highly soluble in cold water and has the CAS number 9003-39-8. The molecular weight of PVP K 30 is about 40000 g/mol.

Other particularly suitable polyvinylpyrrolidones are the substances known under the trade names LUVITEC K 17, LUVITEC K 30, LUVITEC K 60, LUVITEC K 80, LUVITEC K 85, LUVITEC K 90, and LUVITEC K 115 and available from BASF.

The use of film-forming hydrophilic polymers (a3) from the group of copolymers of polyvinylpyrrolidone has also led to particularly good and washfast color results. The storage stabilities of the formulations containing one or more copolymers of polyvinylpyrrolidone (a3) were also particularly good.

Vinylpyrrolidone-vinyl ester copolymers, such as those marketed under the trademark Luviskol® (BASF), are particularly suitable film-forming hydrophilic polymers. Luviskol® VA 64 and Luviskol® VA 73, both vinylpyrrolidone/vinyl acetate copolymers, are particularly preferred non-ionic polymers.

Of the vinylpyrrolidone-containing copolymers, a styrene/VP copolymer and/or a vinylpyrrolidone-vinyl acetate copolymer and/or a VP/DMAPA acrylates copolymer and/or a VP/vinyl caprolactam/DMAPA acrylates copolymer are particularly preferred in cosmetic compositions.

Vinylpyrrolidone-vinyl acetate copolymers are marketed under the name Luviskol® VA by BASF SE. For example, a VP/Vinyl Caprolactam/DMAPA Acrylates copolymer is sold under the trade name Aquaflex® SF-40 by Ashland Inc. For example, a VP/DMAPA acrylates copolymer is marketed by Ashland under the name Styleze CC-10 and is a highly preferred vinylpyrrolidone-containing copolymer.

Other suitable copolymers of polyvinylpyrrolidone (c) may also be those obtained by reacting N-vinylpyrrolidone with at least one further monomer from the group consisting of V-vinylformamide, vinyl acetate, ethylene, propylene, acrylamide, vinylcaprolactam, vinylcaprolactone and/or vinyl alcohol.

In another very particularly preferred embodiment, a process as contemplated herein is exemplified in that the agent (a) comprises at least one film-forming polymer (a3) selected from the group consisting of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, very particularly preferred polyvinylpyrrolidone (PVP).

Another fussy copolymer of vinylpyrrolidone is the polymer known under the INCI designation maltodextrin/VP copolymer.

Furthermore, intensively dyed keratin material, especially hair, with particularly good wash fastness could be obtained if a non-ionic, film-forming, hydrophilic polymer was used as the film-forming, hydrophilic polymer.

In a very particularly preferred embodiment, an agent (a) as contemplated herein is exemplified in that it comprises at least one nonionic, film-forming, hydrophilic polymer (a3).

As contemplated herein, a non-ionic polymer is understood to be a polymer which in a protic solvent—such as water—under standard conditions does not carry structural units with permanent cationic or anionic groups, which must be compensated by counterions while maintaining electron neutrality. Cationic groups include quaternized ammonium groups but not protonated amines Anionic groups include carboxylic and sulphonic acid groups.

Preference is given to products containing, as a non-ionic, film-forming, hydrophilic polymer, at least one polymer selected from the group including Polyvinylpyrrolidone,
Copolymers of N-vinylpyrrolidone and vinyl esters of carboxylic acids having 2 to 18 carbon atoms of N-vinylpyrrolidone and vinyl acetate,
Copolymers of N-vinylpyrrolidone and N-vinylimidazole and methacrylamide,
Copolymers of N-vinylpyrrolidone and N-vinylimidazole and acrylamide,
Copolymers of N-vinylpyrrolidone with N,N-di(C1 to C4)-alkylamino-(C2 to C4)-alkylacrylamide, If copolymers of N-vinylpyrrolidone and vinyl acetate are used, it is again preferable if the molar ratio of the structural units contained in the monomer N-vinylpyrrolidone to the structural units of the polymer contained in the monomer vinyl acetate is in the range from about 20 to about 80 to about 80 to about 20, in particular from about 30 to about 70 to about 60 to about 40. Suitable copolymers of vinyl pyrrolidone and vinyl acetate are available, for example, under the trademarks Luviskol® VA 37, Luviskol® VA 55, Luviskol® VA 64 and Luviskol® VA 73 from BASF SE.

Another particularly preferred polymer is selected from the INCI designation VP/Methacrylamide/Vinyl Imidazole Copolymer, which is available under the trade name Luviset Clear from BASF SE.

Another particularly preferred non-ionic, film-forming, hydrophilic polymer is a copolymer of N-vinylpyrrolidone and N,N-dimethylaminiopropylmethacrylamide, which is sold under the INCI designation VP/DMAPA Acrylates Copolymer e.g., under the trade name Styleze® CC 10 by ISP.

A cationic polymer of interest is the copolymer of N-vinylpyrrolidone, N-vinylcaprolactam, N-(3-dimethylaminopropyl)methacrylamide and 3-(methacryloylamino)propyl-lauryl-dimethylammonium chloride (INCI designation): Polyquaternium-69), which is marketed, for example, under the trade name AquaStyle® 300 (28-32 wt. % active substance in ethanol-water mixture, molecular weight 350000) by ISP.

Other suitable film-forming, hydrophilic polymers include

Vinylpyrrolidone-vinylimidazolium methochloride copolymers, as offered under the designations Luviquat® FC 370, FC 550 and the INCI designation Polyquaternium-16 as well as FC 905 and HM 552,
Vinylpyrrolidone-vinylcaprolactam-acrylate terpolymers, as they are commercially available with acrylic acid esters and acrylic acid amides as a third monomer component, for example under the name Aquaflex® SF 40.

Polyquaternium-11 is the reaction product of diethyl sulphate with a copolymer of vinyl pyrrolidone and dimethylaminoethyl methacrylate. Suitable commercial products are available under the names Dehyquart® CC 11 and Luviquat® PQ 11 PN from BASF SE or Gafquat 440, Gafquat 734, Gafquat 755 or Gafquat 755N from Ashland Inc.

Polyquaternium-46 is the reaction product of vinylcaprolactam and vinylpyrrolidone with methylvinylimidazolium methosulfate and is available for example under the name Luviquat® Hold from BASF SE. Polyquaternium-46 is preferably used in an amount of about 1 to about 5% by weight-based on the total weight of the cosmetic composition. It particularly prefers to use polyquaternium-46 in combination with a cationic guar compound. It is even highly preferred that polyquaternium-46 is used in combination with a cationic guar compound and polyquaternium-11.

Suitable anionic film-forming, hydrophilic polymers can be, for example, acrylic acid polymers, which can be in non-crosslinked or crosslinked form. Such products are sold commercially under the trade names Carbopol 980, 981, 954, 2984 and 5984 by Lubrizol or under the names Synthalen M and Synthalen K by 3V Sigma (The Sun Chemicals, Inter Harz).

Examples of suitable film-forming, hydrophilic polymers from the group of natural gums are xanthan gum, gellan gum, carob gum.

Examples of suitable film-forming hydrophilic polymers from the group of polysaccharides are hydroxyethyl cellulose, hydroxypropyl cellulose, ethyl cellulose and carboxymethyl cellulose.

Suitable film-forming, hydrophilic polymers from the acrylamide group are, for example, polymers prepared from monomers of (methy)acrylamido-C1-C4-alkyl-sulfonic acid or salts thereof. Corresponding polymers may be selected from the polymers of polyacrylamidomethanesulfonic acid, polyacrylamidoethanesulfonic acid, polyacrylamidopropanesulfonic acid, poly2-acrylamido-2-methylpropanesulfonic acid, poly-2-methylacrylamido-2-methylpropanesulfonic acid and/or poly-2-methylacrylamido-n-butanesulfonic acid.

Preferred polymers of the poly(meth)arylamido-C1-C4-alkyl sulphonic acids are cross-linked and at least 90% neutralized. These polymers can or cannot be cross-linked.

Cross-linked and totally or partially neutralized polymers of the poly-2-acrylamido-2-methylpropane sulphonic acid type are known under the INCI designation "Ammonium Polyacrylamido-2-methyl propanesulphonates" or "Ammonium Polyacryldimethyltauramides".

Another preferred polymer of this type is the cross-linked poly-2-acrylamido-2-methyl-propanesulphonic acid polymer marketed by Clamant under the trade name Hostacerin AMPS, which is partially neutralized with ammonia.

The film-forming polymer or polymers (a3) as contemplated herein are preferably used in certain ranges of amounts in the composition as contemplated herein. In this context, it has proved particularly preferable for solving the problem as contemplated herein if the agent (a) contains—based on the total weight of the agent (a)—one or more film-forming polymers (a3) in a total amount of from about 0.1 to about 25.0% by weight, preferably from about 0.2 to about 20.0% by weight, more preferably from about 0.5 to about 15.0% by weight and very particularly preferably from about 1.0 to about 7.0% by weight.

pH Value of the Agent (a)

The colorant (a) is preferably adjusted to a neutral to alkaline pH value. Very preferably, the colorant (a) is adjusted to an alkaline pH value. Under basic conditions, the amino-functionalized silicone polymer (a1) can be dissolved or dispersed particularly well and without protonation.

To adjust the desired pH value, the agent (a) preferably contains at least one alkalizing agent. The pH values for the purposes of the present disclosure are pH values measured at a temperature of 22° C.

As alkalizing agent, agent (a) may contain, for example, ammonia, alkanolamines and/or basic amino acids.

The alkanolamines which can be used in the composition of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore exemplified in that the agent as contemplated herein contains an alkanolamine selected from 2-aminoethan-1-ol and/or 2-amino-2-methylpropan-1-ol as alkalizing agent.

An amino acid in the context of the present disclosure is an organic compound which in its structure contains at least one protonatable amino group and at least one —COOH or one —SO3H group. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine, and histidine, especially preferably arginine and lysine. In another particularly preferred embodiment, an agent as contemplated herein is therefore exemplified in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly preferred alkalizing agents are ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-Amino-2-methylpropan-2-ol, 3-aminopropan-1,2-diol, 2-amino-2-methylpropan-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

In another very particularly preferred embodiment, a process as contemplated herein is exemplified in that the colorant (a) comprises at least one alkalizing agent selected from the group consisting of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Particularly good results were obtained when agent (a) was adjusted to a pH value of about 7.0 to about 11.5 preferably from about 8.0 to about 11.0, and especially preferably from about 8.5 to about 10.5.

In another very particularly preferred embodiment, a process as contemplated herein is exemplified in that the agent (a) comprises water and has a pH value of from about 7.0 to about 11.5 preferably from about 8.0 to about 11.0, and particularly preferably from about 8.5 to about 10.5.

Acid (b1) on Average (b)

Following the application of the coloring agent (a) on the keratin material, the post-treatment agent (b) is applied. The aftertreatment agent (b) is an acid-adjusted solution, dispersion, or emulsion. As an ingredient essential to the present disclosure, the aftertreatment agent (b) therefore contains at least one acid (b1)

Certain acids have proven to be particularly suitable for adjusting the desired pH value. These acids may be selected, for example, from the group consisting of citric acid, tartaric acid, malic acid, lactic acid, acetic acid, methanesulfonic acid, benzoic acid, malonic acid, oxalic acid, 1-hydroxyethane-1,1-diphosphonic acid, sulfuric acid, hydrochloric acid, and phosphoric acid.

In another very particularly preferred embodiment, a process as contemplated herein is exemplified in that the agent (b) comprises at least one acid (b1) selected from the group consisting of citric acid, tartaric acid, malic acid, lactic acid, acetic acid, methanesulfonic acid, benzoic acid, malonic acid, oxalic acid, 1-hydroxyethane-1,1-diphosphonic acid, sulfuric acid, hydrochloric acid, and phosphoric acid.

As soon as the aftertreatment agent (b) is applied, it meets the amino silicones (a1), and colorant compounds (a2) deposited on the keratin material. Since the agent (b) is acidic, it also lowers the pH in the immediate vicinity of the amino silicone (a1). In this context, it is assumed that the reduction in pH results in a protonation of the amino silicone (a1), because of which adhesion forces to the keratin material are further strengthened and the colorant compounds (a2) are even more strongly bound to the hair. This massively improves the wash fastness of the resulting dyeing. For this reason, the aftertreatment agent (b) is preferably adjusted to an acidic pH value in the range from about 1.5 to about 5.5 preferably from about 2.0 to about 4.8, and particularly preferably from about 2.5 to about 4.5.

In another very particularly preferred embodiment, a process as contemplated herein is exemplified in that the agent (b) comprises water and has a pH value of from about 1.5 to about 5.5 preferably from about 2.0 to about 4.8, and particularly preferably from about 2.5 to about 4.5.

In the course of the work leading to the present disclosure, the choice of the time at which the pH value is lowered has been found to be essential to produce stable layers on the keratin material. It is essential to the present disclosure that the pH value of the amino silicone (a1) is lowered after it has been applied to the keratin fiber. When amino silicone (a1) and acid are applied simultaneously, there is no significant enhancement of binding to keratin. For this reason, it is essential to the present disclosure to incorporate the acid (b1) into the aftertreatment agent (b).

It was found that the more the pH value was lowered in the vicinity of the amino silicone (a1), the greater the improvement in wash fastness. In other words, the colorations were particularly stable when the colorant (a) was comparatively strongly alkaline and the aftertreatment agent (b) had a relatively acidic pH value.

Film-Forming Polymer (b2) in the Medium (b)

In the process as contemplated herein, there is the proviso that at least one of the agents (a) and/or (b) used in the process contains a film-forming polymer. If the film-forming polymer is contained in the post-treatment agent (b), this is referred to as (b2).

The film-forming polymers contained in agent (b) may be the same as those already described in connection with agent (a).

For example, the aftertreatment agent (b) may include a film-forming polymer (b2) selected from the group consisting of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, very particularly preferred polyvinylpyrrolidone (PVP).

In addition, the aftertreatment agent (b) may also contain a film-forming polymer selected from the group including copolymers of acrylic acid, copolymers of methacrylic acid, homopolymers or copolymers of acrylic acid esters, homopolymers or copolymers of methacrylic acid esters, homopolymers or copolymers of acrylic amides homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

Film-forming polymers selected from the group of synthetic polymers, polymers obtainable by free-radical polymerization or natural polymers have proved particularly suitable for solving the problem as contemplated herein.

Other particularly well-suited film-forming polymers can be selected from the homopolymers or copolymers of olefins, such as cycloolefins, butadiene, isoprene or styrene, vinyl ethers, vinyl amides, the esters, or amides of (meth)acrylic acid having at least one $C_1$-$C_{20}$ alkyl group, an aryl group or a C2-C10 hydroxyalkyl group.

Other film-forming polymers may be selected from the homo- or copolymers of isooctyl (meth)acrylate; isononyl (meth)acrylate; 2-ethylhexyl (meth)acrylate; lauryl (meth)acrylate); isopentyl (meth)acrylate; n-butyl (meth)acrylate); isobutyl (meth)acrylate; ethyl (meth)acrylate; methyl (meth)acrylate; tert-butyl (meth)acrylate; stearyl (meth)acrylate; hydroxyethyl (meth)acrylate; 2-hydroxypropyl (meth)acrylate; 3-hydroxypropyl (meth)acrylate; and/or mixtures thereof.

Further film-forming polymers may be selected from the homo- or copolymers of (meth)acrylamide; N-alkyl-(meth)acrylamides, in those with C2-C18 alkyl groups, such as N-ethyl-acrylamide, N-tert-butyl-acrylamide, 1e N-octylcrylamide; N-di(C1-C4)alkyl-(meth)acrylamide.

Other preferred anionic copolymers are, for example, copolymers of acrylic acid, methacrylic acid or their $C_1$-$C_6$ alkyl esters, as they are marketed under the INCI Declaration Acrylates Copolymers. A suitable commercial product is for example Aculyn® 33 from Rohm & Haas. Copolymers of acrylic acid, methacrylic acid or their $C_1$-$C_6$ alkyl esters and the esters of an ethylenically unsaturated acid and an alkoxylated fatty alcohol are also preferred. Suitable ethylenically unsaturated acids are especially acrylic acid, methacrylic acid and itaconic acid; suitable alkoxylated fatty alcohols are especially steareth-20 or ceteth-20.

Very particularly preferred polymers on the market are, for example, Aculyn®22 (Acrylates/Steareth-20 Me-thacrylate Copolymer), Aculyn® 28 (Acrylates/Beheneth-25 Methacrylate Copolymer), Structure 2001® (Acrylates/Steareth-20 Itaconate Copolymer), Structure 3001® (Acrylates/Ceteth-20 Itaconate Copolymer), Structure Plus® (Acrylates/Aminoacrylates C10-30 Alkyl PEG-20 Itaconate Copolymer), Carbopol® 1342, 1382, Ultrez 20, Ultrez 21 (Acrylates/C10-30 Alkyl Acrylate Crosspolymer), Synthalen W 2000® (Acrylates/Palmeth-25 Acrylate Copolymer) or the Rohme and Haas distributed Soltex OPT (Acrylates/C12-22 Alkyl methacrylate Copolymer).

The homo- and copolymers of N-vinylpyrrolidone, vinylcaprolactam, vinyl-(C1-C6)alkyl-pyrrole, vinyl-oxazole, vinyl-thiazole, vinylpyrimidine, vinylimidazole can be named as suitable polymers based on vinyl monomers.

Furthermore, the copolymers octylacrylamide/acrylates/butylaminoethyl-methacrylate copolymer, as commercially marketed under the trade names AMPHOMER® or LOVOCRYL® 47 by NATIONAL STARCH, or the copolymers of acrylates/octylacrylamides marketed under the trade names DERMACRYL® LT and DERMACRYL® 79 by NATIONAL STARCH are particularly suitable.

Suitable olefin-based polymers include homopolymers and copolymers of ethylene, propylene, butene, isoprene and butadiene.

In another version, block copolymers can be used as film-forming hydrophobic polymers, which comprise at least one block of styrene or the derivatives of styrene. These block copolymers can be copolymers that contain one or more other blocks in addition to a styrene block, such as styrene/ethylene, styrene/ethylene/butylene, styrene/butylene, styrene/isoprene, styrene/butadiene. Such polymers are commercially distributed by BASF under the trade name "Luvitol HSB".

In another very particularly preferred embodiment, a process as contemplated herein is exemplified in that the aftertreatment agent (b) comprises at least one film-forming polymer (b2) selected from the group consisting of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, the copolymers of acrylic acid, of copolymers of methacrylic acid, of homopolymers or copolymers of acrylic acid esters, of homopolymers or copolymers of methacrylic acid esters, of homopolymers or copolymers of acrylic acid amides, of homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters and/or polyamides.

The film-forming polymer or polymers are preferably used in certain ranges of amounts in the aftertreatment agent (b). In this context, it has proved to be particularly preferred for the solution of the task as contemplated herein if the agent (b)—based on the total weight of agent (b)—contains one or more polymers in a total amount of about 0.1 to about 25.0% by weight, preferably from about 0.2 to about 20.0% by weight, more preferably from about 0.5 to about 15.0% by weight and very particularly preferably from about 1.0 to about 7.0% by weight.

Other Ingredients in Products (a) and (b)

The agents (a) and (b) described above may also contain one or more optional ingredients.

The products may also contain one or more surfactants. The term surfactants refer to surface-active substances. A distinction is made between anionic surfactants consisting of a hydrophobic residue and a negatively charged hydrophilic head group, amphoteric surfactants, which carry both a negative and a compensating positive charge, cationic surfactants, which in addition to a hydrophobic residue have a positively charged hydrophilic group, and non-ionic surfactants, which have no charges but strong dipole moments and are strongly hydrated in aqueous solution.

Zwitterionic surfactants are those surface-active compounds which carry at least one quaternary ammonium group and at least one —$COO^{(-)}$— or —$SO_3^{(-)}$ group in the molecule. Particularly suitable zwitterionic surfactants are the so-called betaines such as the N-alkyl-N,N-dimethylammonium-glycinate, for example the cocoalkyl-dimethylammoniumglycinate, N-acylaminopropyl-N,N-dimethylammoniumglycinate, for example, cocoacylaminopropyl dimethyl ammonium glycinate, and 2-alkyl-3-carboxymethyl-3-hydroxyethyl imidazolines each having 8 to 18 C atoms in the alkyl or acyl group, and cocoacylaminoethyl hydroxyethyl carboxymethyl glycinate. A preferred zwitterionic surfactant is the fatty acid amide derivative known under the INCI name cocamidopropyl betaine.

Ampholytic surfactants are surface-active compounds which, apart from a $C_8$-$C_{24}$ alkyl or acyl group, contain at least one free amino group and at least one —COOH— or —$SO_3H$ group in the molecule and can form internal salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids each with about 8 to 24 C atoms in the alkyl group. Typical examples of amphoteric or zwitterionic surfactants are alkylbetaines, alkylamidobetaines, amino propionates, aminoglycinate, imidazoliniumbetaines and sulfobetaines.

Particularly preferred ampholytic surfactants are N-cocoalkylaminopropionate, cocoacylaminoethylaminopropionate and $C_{12}$-$C_{18}$ acylsarcosine.

The products may also additionally contain at least one non-ionic surfactant. Suitable non-ionic surfactants are alkyl polyglycosides as well as alkylene oxide addition products to fatty alcohols and fatty acids with 2 to 30 mol ethylene oxide per mol fatty alcohol or fatty acid. Preparations with good properties are also obtained if they contain as non-ionic surfactants fatty acid esters of ethoxylated glycerol reacted with at least 2 mol ethylene oxide. The non-ionic surfactants are used in a total quantity of about 0.1 to about 45% by weight, preferably from about 1 to about 30% by weight and very preferably from about 1 to about 15% by weight-based on the total weight of the respective agent.

In addition, the products may also contain at least one cationic surfactant. Cationic surfactants are surfactants, i.e., surface-active compounds, each with one or more positive charges. Cationic surfactants contain only positive charges. Usually, these surfactants are composed of a hydrophobic part and a hydrophilic head group, the hydrophobic part usually consisting of a hydrocarbon backbone (e.g., consisting of one or two linear or branched alkyl chains) and the positive charge(s) being in the hydrophilic head group. Examples of cationic surfactants are quaternary ammonium compounds which, as hydrophobic radicals, may carry one or two alkyl chains with a chain length of 8 to 28 C atoms, quaternary phosphonium salts substituted with one or more alkyl chains with a chain length of 8 to 28 C atoms or tertiary sulfonium salts.

Furthermore, the cationic charge can also be part of a heterocyclic ring (e.g., an imidazolium ring or a pyridinium ring) in the form of an onium structure. In addition to the functional unit carrying the cationic charge, the cationic surfactant may also contain other uncharged functional groups, as is the case for example with esterquats. The cationic surfactants are used in a total quantity of about 0.1 to about 45 wt. %, preferably from about 1 to about 30 wt. % and most preferably from about 1 to about 15 wt. %—based on the total weight of the respective agent.

Furthermore, the means as contemplated herein may also contain at least one anionic surfactant. Anionic surfactants are surface-active agents with exclusively anionic charges (neutralized by a corresponding counter cation). Examples of anionic surfactants are fatty acids, alkyl sulphates, alkyl ether sulphates and ether carboxylic acids with 12 to 20 C atoms in the alkyl group and up to 16 glycol ether groups in the molecule.

The anionic surfactants are used in a total quantity of about 0.1 to about 45 wt. %, preferably from about 1 to about 30 wt. % and most preferably about 1 to about 15 wt. %—based on the total weight of the respective agent.

They may also contain other active substances, auxiliaries and additives, such as solvents, fatty components such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; polymers, structural agents such as glucose, maleic acid and lactic acid; hair conditioning compounds such as phospholipids, for example lecithin and cephalins; perfume oils, dimethylisosorbide and cyclodextrins; fiber structure-improving active substances, in particular mono-, di- and oligosaccharides such as glucose, galactose, fructose, fructose and lactose; dyes for coloring the composition; anti-dandruff active substances such as Piroctone Olamine, Zinc Omadine and Climbazol; amino acids and oligopeptides; protein hydrolysates on animal and/or vegetable basis, as well as in the form of their fatty acid condensation products or optionally anionic or cationically modified derivatives; vegetable oils; sunscreens and UV-blockers; active ingredients such as panthenol, pantothenic acid, pantolactone, allantoin, pyrrolidinonecarboxylic acids and their salts, and bisabolol; polyphenols, in particular hydroxycinnamic acids, 6,7-dihydroxycumarine, hydroxybenzoic acids, catechine, tannine, leukoanthocyanidine, anthocyanidine, flavanone, flavone and flavonols; ceramides or pseudoceramides; vitamins, provitamins and vitamin precursors; plant extracts; fats and waxes such as fatty alcohols, beeswax, montan wax and paraffins; swelling and penetrating substances such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescent agents such as ethylene glycol mono- and distearate and PEG-3 distearate; and blowing agents such as propane-butane mixtures, $N_2O$, dimethyl ether, $CO_2$ and air.

The selection of these other substances will be made by the specialist according to the desired properties of the agents. Regarding other optional components and the quantities of these components used, explicit reference is made to the relevant manuals known to the specialist. The additional active ingredients and auxiliary substances are preferably used in the preparations as contemplated herein in quantities of about 0.0001 to about 25 wt. % each, of about 0.0005 to about 15 wt. %, based on the total weight of the respective agent.

Process for Dyeing Keratin Materials

In the procedure as contemplated herein, agents (a) and (b) are applied to the keratinous materials, to human hair. The agent (b) is an after-treatment agent and is therefore applied after dyeing agent (a).

Therefore, a method for dyeing keratinous material, in particular human hair, comprising the following steps in the order given is particularly preferred:

in a first step, applying a coloring agent (a) to the keratinous material, said agent comprising (a):
  (a1) at least one amino-functionalized silicone polymer, and
  (a2) at least one color-imparting compound, and
  (a3) optionally at least one film-forming polymer which is different from (a1), and in a second step, applying a post-treatment agent (b) to the keratinous material, the agent comprising (b):
  (b1) at least one acid, and
  (b2) optionally at least one film-forming polymer, with the proviso that at least one of the agents (a) and/or (b) comprises at least one film-forming polymer.

The agents (a) and (b) are particularly preferably applied within one and the same dyeing process, which means that there is a period of a maximum of several hours between the application of agents (a) and (b).

In a further preferred embodiment, a method as contemplated herein is exemplified in that first the agent (a) is applied, and then the agent (b) is applied, the time between the application of the agents (a) and (b) being at most 24 hours, preferably at most 12 hours and particularly preferably at most 6 hours.

In the process as contemplated herein, the keratin materials, in particular human hair, are first treated with colorant (a). Subsequently, the aftertreatment agent (b) is applied to the keratin materials, which lowers the pH value on the surface of the keratin material, thus fixing or immobilizing the active ingredients contained in the agent (a) on the keratin. Preferably, the agent (b) itself does not contain any dyes or color-imparting compounds.

The technical application properties of the resulting dyeing can be further improved by selecting the optimum process conditions.

In the context of a further form of execution, a procedure comprising the following steps in the order indicated is particularly preferred (1) Application of the staining agent (a) on the keratinous material,
(2) Allow the agent (a) to act for a period of 10 seconds to 10 minutes, preferably from 10 seconds to 5 minutes,
(3) if necessary, rinse the keratinous material with water,
(4) Application of the after-treatment agent (b) on the keratinous material,
(5) Allow the agent (b) to act for a period of 30 seconds to 30 minutes, preferably from 30 seconds to 10 minutes, and
(6) Rinse the keratinous material with water.

The rinsing of the keratinous material with water in steps (3) and (6) of the process is understood, as contemplated herein, to mean that only water is used for the rinsing process, without any other agents other than agents (a) and (b).

In a first step (1), agent (a) is applied to the keratin materials, especially human hair.

After application, the agent (a) can act on the keratin materials. The process as contemplated herein permits the production of dyeing with particularly good intensity and wash fastness even with a short contact time of the agent (a). In this context, application times from about 10 seconds to about 10 minutes, preferably from about 20 seconds to about 5 minutes and especially preferably from about 30 seconds to about 2 minutes on the hair have proven to be particularly beneficial.

In a preferred embodiment of the method as contemplated herein, the agent (a) can now be rinsed from the keratin materials before the agent (b) is applied to the hair in the subsequent step.

Dyeing with also good wash fastness were obtained when agent (b) was applied to the keratin materials which were still exposed to agent (a).

In step (4), agent (b) is now applied to the keratin materials. After application, let the agent (b) act on the hair.

The process as contemplated herein permits the production of dyeing with particularly good intensity and wash fastness even with a short contact time of the agent (b). Application times from about 10 seconds to about 10 minutes, preferably from about 20 seconds to about 5 minutes and most preferably from about 30 seconds to about 3 minutes on the hair have proven to be particularly beneficial.

In step (6), agent (b) (and any remaining agent (a)) is rinsed out of the keratin material with water.

In the context of a further form of execution, a procedure comprising the following steps in the order indicated is particularly preferred (1) Application of agent (a) on the keratinous material,
(2) Allow the agent (a) to act for a period of about 10 seconds to about 10 minutes, preferably from about 10 seconds to about 5 minutes,
(3) No rinsing
(4) Application of agent (b) on the keratinous material,
(5) Allow the agent (b) to act for a period of about 30 seconds to about 30 minutes, preferably from about 30 seconds to about 10 minutes, and
(6) Rinse the keratinous material with water.

In this embodiment, the sequence of steps (1) to (6) preferably takes place within 24 hours.

Multi-Component Packaging Unit (Kit-of-Parts)

To increase user comfort, the user is preferably provided with all required resources in the form of a multi-component packaging unit (kit-of-parts).

A second subject of the present disclosure is therefore a multi-component packaging unit (kit-of-parts) for coloring keratinous material, comprehensively packaged separately from one another a first container containing a coloring agent (a), said agent containing (a):
  (a1) at least one amino-functionalized silicone polymer, and
  (a2) at least one color-imparting compound, and
  (a3) optionally at least one film-forming polymer,
a second container containing an agent (b), wherein the agent contains (b):
  (b1) at least one acid,
  (b2) optionally, at least one film-forming polymer,
with the proviso that at least one of the agents (a) and/or (b) contains at least one film-forming polymer,
wherein the ingredients (a1), (a2), (a3), (b1) and (b2) have already been disclosed in detail in the description of the first subject matter of the present disclosure.

The amino-functionalized silicone polymers (a1) contained in agent (a) of the kit correspond to the amino-functionalized silicone polymers (a1) that were also used in agent (a) of the previously described process.

The colorant compounds (a2) contained in the agent (a) of the kit correspond to the colorant compounds (a2) that were also used in the agent (a) of the previously described process.

The film-forming polymers (a3) optionally contained in the agent (a) of the kit, correspond to the film-forming polymers (a3) that were also used in the agent (a) of the previously described process.

The acids (b1) contained in the agent (b) of the kit correspond to the acids (b1) that were also used in the agent (b) of the previously described process.

The film-forming polymers (b2) optionally contained in the agent (b) of the kit, correspond to the film-forming polymers (b2) that were also used in the agent (a) of the previously described process.

With respect to the other preferred embodiments of the multi-component packaging unit as contemplated herein, the same applies mutatis mutandis to the procedure as contemplated herein.

EXAMPLES

1. Formulations

The following formulations were prepared (all FIGURES are in wt % unless otherwise stated).

Dyeing Agent (a)

| Agent (a) | (aV) Comparison | (aE) Present Disclosure |
|---|---|---|
| Cetrimonium chloride | 3.3 | 3.3 |
| Stearamidopropyldimethylamine | 1.0 | 1.0 |
| Phenoxyethanol | 0.4 | 0.4 |
| Methyl paraben | 0.3 | 0.3 |
| Dimethicone 5 cst | 5.0 | 5.0 |
| Dimethicone 60000 cst | 1.0 | 1.0 |
| Luviscol K30 (BASF, Polyvinylpyrrolidone) | 5.0 | 5.0 |
| Lavanya Zuni (organic pigment, Neelikon Red, 111P0200, CI 12490) | 0.5 | 0.5 |
| Dow Corning 2-8566 (Siloxanes and Silicones, 3-[(2-Aminoethyl)amino]-2-methylpropyl Me, Di-Me-Siloxane" | 0.50 | 0.50 |
| 1.2-propanediol | 0.25 | 0.25 |
| Ammonia | — | ad pH 9.0 |
| Citric acid | ad pH 3.0 | — |
| Water | ad 100 | ad 100 |

After-Treatment Agent (b)

| Agent (b) | (bV) Comparison | (bE) Present Disclosure |
|---|---|---|
| Citric acid | — | ad pH 3.0 |
| Water | ad 100 | ad 100 |

2. Application

Agent (a) was applied to one strand of hair at a time (Kerling, Euronatural hair white, liquor ratio: 4 g of agent (a) per g of hair strand) applied and then left to act for one minute. The hair strand was then dipped into the post-treatment agent (b) and left in it for 1 minute. Subsequently, each hair strand was thoroughly washed (1 minute) with water, dried, and visually evaluated under the daylight lamp.

To determine wash fastness, previously dyed hair strands were placed in an ultrasonic bath filled with a 1% solution of a commercial shampoo (foams, 7 herbs). Then the hair strands were treated with ultrasound according to a standardized procedure corresponding to 6 hair washes. After this period, the strands were removed from the ultrasonic bath, dried, and visually assessed again under the daylight lamp.

| | Application | Application |
|---|---|---|
| Dyeing agent (a) | (aV) | (aE) |
| After-treatment agent (b) | (bV) | (bE) |
| Coloring | reddish | red |
| Color Intensity (directly after staining) | ++ | +++ |
| Color intensity (after 6 hair washes9 | + | +++ |

Color intensity: −= uncolored += low ++= average +++= very good

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A process for dyeing keratinous material comprising the following steps:
    applying a coloring agent (a) to the keratinous material, the agent (a) comprising:
        (a1) at least one amino-functionalized silicone polymer, and
        (a2) at least one color-imparting compound, and
        (a3) optionally, a film-forming polymer different from (a1),
    applying a post-treatment agent (b) to the keratinous material, the agent (b) comprising:
        (b 1) at least one acid, and
        (b2) optionally, a film-forming polymer,
    with the proviso that at least one of the agents (a) and/or (b) comprises at least one film-forming polymer.

2. The process according to claim 1, wherein the agent (a) comprises at least one amino-functionalized silicone polymer (a1) having at least one secondary amino group.

3. The process according to claim 1 wherein the agent (a) comprises at least one amino-functionalized silicone polymer (a1) comprising at least one structural unit of the formula (Si-Amino),

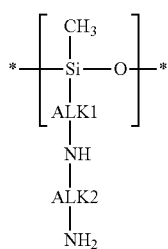

(Si-Amino)

where ALK1 and ALK2 independently represent a linear or branched $C_1$-$C_{20}$ divalent alkylene group.

4. The process according to claim 1 wherein the agent (a) comprises at least one amino-functionalized silicone polymer (a1) comprising structural units of the formula (Si-I) and of the formula (Si-II)

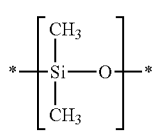

(Si-I)

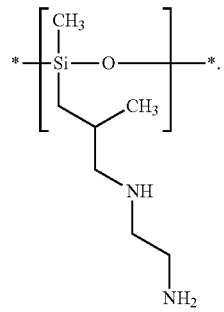

(Si-II)

5. The process according to claim 1 wherein the agent (a) comprises—based on the total weight of the agent (a)—one or more amino-functionalized silicone polymers in a total amount of from about 0.1 to about 8.0% by weight.

6. The process according to claim 1, wherein the agent (a) comprises at least one colorant compound (a2) selected from the group consisting of pigments, direct dyes, photochromic dyes, and thermochromic dyes.

7. The process according to claim 1, wherein the agent (a) comprises at least one colorant compound (a2) selected from the group of inorganic pigments selected from the group of colored metal oxides, metal hydroxides, metal oxide hydrates, silicates, metal sulfides, complex metal cyanides, metal sulfates, bronze pigments, and/or from colored mica- or mica-based pigments coated with at least one metal oxide and/or a metal oxychloride.

8. The process according to claim 1 wherein the composition (a) comprises at least one colorant compound (a2) selected from the group of organic pigments selected from the group consisting of carmine, quinacridone, phthalocyanine, sorghum, blue pigments with the color index numbers Cl 42090, CI 69800, CI 69825, CI 73000, CI 74100, CI 74160, yellow pigments with the color index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

9. The process according to claim 1 wherein the agent (a) comprises at least one coloring compound (a2) selected from the group consisting of anionic, nonionic, and cationic direct dyes.

10. The process according to claim 1 wherein the agent (a) comprises at least one nonionic, film-forming, hydrophilic polymer (a3).

11. The process according to claim 1 wherein the agent (a) comprises at least one film-forming polymer (a3) selected from the group consisting of polyvinylpyrrolidone (PVP) and the copolymers of polyvinylpyrrolidone.

12. The process according to claim 1 wherein the agent (a) comprises at least one film-forming polymer (a3) selected from the group consisting of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers, and/or vinylpyrrolidone/vinyl alcohol copolymers.

13. The process according to claim 1 wherein the colorant (a) comprises at least one alkalizing agent selected from the group consisting of ammonia, 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropane-1,2-diol, 2-amino-2-methylpropane-1,3-diol, arginine, lysine, ornithine, histidine, sodium hydroxide, potassium hydroxide, calcium hydroxide, barium hydroxide, sodium phosphate, potassium phosphate, sodium silicate, sodium metasilicate, potassium silicate, sodium carbonate, and potassium carbonate.

14. The process according to claim 1 wherein the agent (a) comprises water and has a pH of from about 7.0 to about 11.5.

15. The process according to claim 1 wherein the agent (b) comprises at least one acid (b1) selected from the group consisting of citric acid, tartaric acid, malic acid, lactic acid, acetic acid, methanesulfonic acid, benzoic acid, malonic acid, oxalic acid, 1-hydroxyethane-1,1-diphosphonic acid, sulfuric acid, hydrochloric acid, and phosphoric acid.

16. The process according to claim 1 wherein the agent (b) comprises water and has a pH of from about 1.5 to about 5.5.

17. The process according to claim 1 wherein the after-treatment agent (b) comprises at least one film-forming polymer (b2) selected from the group consisting of polyvinylpyrrolidone (PVP), vinylpyrrolidone/vinyl acetate copolymers, vinylpyrrolidone/styrene copolymers, vinylpyrrolidone/ethylene copolymers, vinylpyrrolidone/propylene copolymers, vinylpyrrolidone/vinylcaprolactam copolymers, vinylpyrrolidone/vinylformamide copolymers and/or vinylpyrrolidone/vinyl alcohol copolymers, the copolymers of acrylic acid, of copolymers of methacrylic acid, of homopolymers or copolymers of acrylic acid esters, of homopolymers or copolymers of methacrylic acid esters, of homopolymers or copolymers of acrylic acid amides, of homopolymers or copolymers of methacrylic acid amides, copolymers of vinylpyrrolidone, copolymers of vinyl alcohol, copolymers of vinyl acetate, homopolymers or copolymers of ethylene, homopolymers or copolymers of propylene, homopolymers or copolymers of styrene, polyurethanes, polyesters, and/or polyamides.

18. The process according to claim 1 wherein first the agent (a) is applied, then the agent (b) is applied, the period between the application of the agents (a) and (b) being at most 24 hours.

19. The process according to claim 1, comprising the following steps in the order indicated,
(1) applying the staining agent (a) on the keratinous material,
(2) allowing the agent (a) to act for a period of about 10 seconds to about 10 minutes,
(3) if necessary, rinsing the keratinous material with water,
(4) applying the after-treatment agent (b) on the keratinous material,
(5) allowing the agent (b) to act for a period of about 30 seconds to about 30 minutes, and
(6) rinsing the keratinous material with water.

* * * * *

UNITED STATES PATENT AND TRADEMARK OFFICE
CERTIFICATE OF CORRECTION

| | |
|---|---|
| PATENT NO. | : 11,529,303 B2 |
| APPLICATION NO. | : 17/415618 |
| DATED | : December 20, 2022 |
| INVENTOR(S) | : Marc Nowottny, Torsten Lechner and Sofie Baumann |

It is certified that error appears in the above-identified patent and that said Letters Patent is hereby corrected as shown below:

In the Specification

Column 12, Line 48 change "$Si(CH_3)_2CH_3$" to --$Si(CH_3)_2OCH_3$--.
Column 19, Line 52 change "((4-sulfophenyeazo)" to --((4-sulfophenyl)azo)--.

Signed and Sealed this
Twenty-first Day of November, 2023

Katherine Kelly Vidal
*Director of the United States Patent and Trademark Office*